US00PP34022P3

(12) United States Plant Patent
Schoone

(10) Patent No.: US PP34,022 P3
(45) Date of Patent: Mar. 15, 2022

(54) **X *DORITAENOPSIS* PLANT NAMED 'UNTOLD STORIES'**

(50) Latin Name: **x *Doritaenopsis* (*Doritis* x *Phalaenopsis*)**
Varietal Denomination: Untold Stories

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/340,016

(22) Filed: Jun. 5, 2021

(65) Prior Publication Data

US 2021/0386004 P1 Dec. 9, 2021

Related U.S. Application Data

(60) Provisional application No. 62/705,005, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Doritaenopsis* plant named 'Untold Stories', characterized by its upright plant habit; moderately vigorous to vigorous growth habit; strong flowering stems; strong leaves; freely flowering habit with typically two inflorescences per plant, each inflorescence with numerous flowers; flowers with fused labella; white-colored flowers that are densely covered with variable and coalescing dark red to purplish red-colored blotches and spots; and good postproduction longevity.

2 Drawing Sheets

Figure 1:
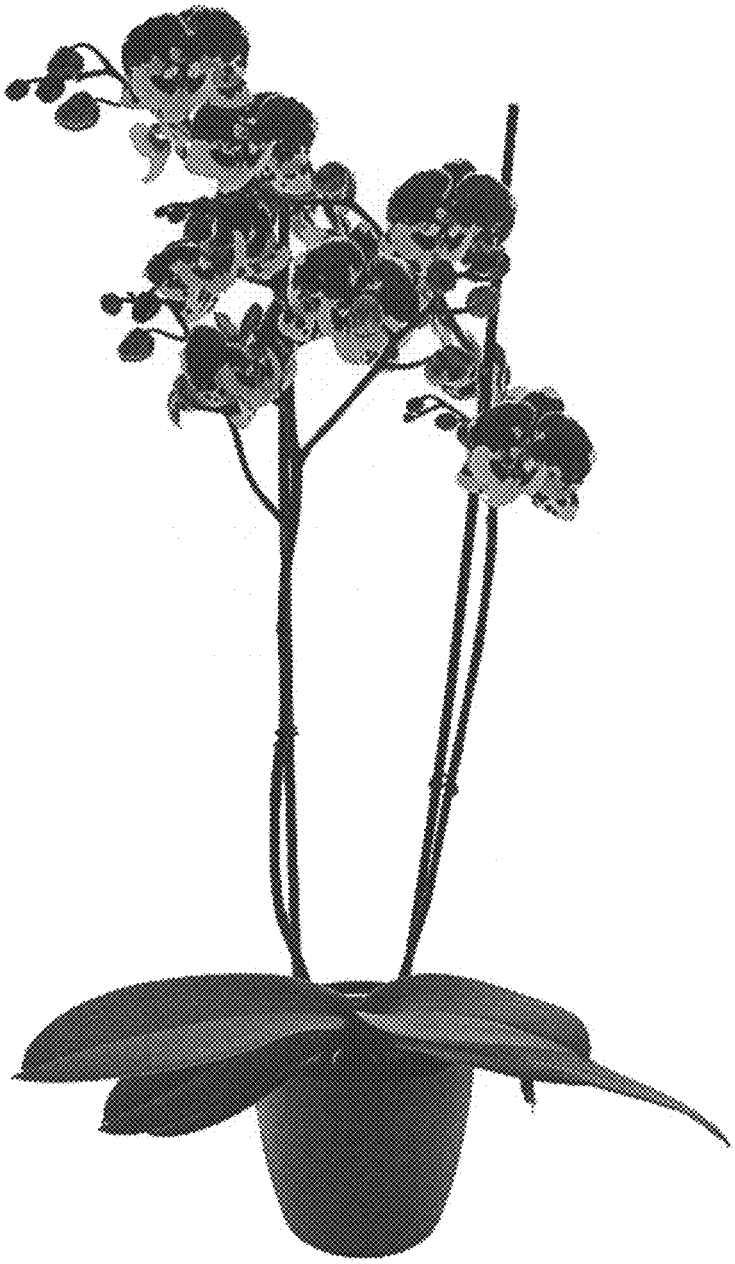

Botanical designation: x *Doritaenopsis* (*Doritis* x *Phalaenopsis*).
Cultivar denomination: 'UNTOLD STORIES'.

CROSS-REFERENCED TO CLOSELY-RELATED APPLICATIONS

Title: Varieties of *Doritaenopsis* Plants
Inventor: René Schoone
Filed: Jun. 6, 2020
Serial number: Ser. No. 62/705,005
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Apr. 23, 2020, application number 2020/1110. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of x *Doritaenopsis* plant, botanically known as x *Doritaenopsis* (*Doritis* x *Phalaenopsis*), commonly referred to as *Doritaenopsis* and hereinafter referred to by the name 'Untold Stories'.

The new *Doritaenopsis* plant is a product of a planned breeding program conducted by the Inventor in Nantou, Taiwan and Heemskerk, The Netherlands. The objective of the breeding program is to develop new fast-growing and freely flowering *Doritaenopsis* plants with good leaf shape and large flowers with unique and attractive patterns and coloration.

The new *Doritaenopsis* plant originated from a cross-pollination in May, 2012 in Nantou, Taiwan of x *Doritaenopsis* 'Mei Dar Diamond', not patented, as the female, or seed, parent with x *Doritaenopsis* 'Luchia Pink', not patented, as the male, or pollen, parent. The new *Doritaenopsis* plant was discovered and selected by the Inventor as a single flowering plant from within the progeny of the stated cross-pollination grown in a controlled greenhouse environment in Heemskerk, The Netherlands in April, 2017.

Asexual reproduction of the new *Doritaenopsis* plant by in vitro meristem propagation in a controlled environment in Assendelft, The Netherlands since April, 2018 has shown that the unique features of this new *Doritaenopsis* plant are stable and reproduced true to type in successive generations.

SUMMARY OF THE INVENTION

Plants of the new *Doritaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Untold Stories'. These characteristics in combination distinguish 'Untold Stories' as a new and distinct *Doritaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Flowers with fused labella, typically referred to as a "big lip" type.
7. White-colored flowers that are densely covered with variable and coalescing dark red to purplish red-colored blotches and spots, also referred to as "cow spots".
8. Good postproduction longevity.

Plants of the new *Doritaenopsis* can be compared to plants of the female parent, 'Mei Dar Diamond'. Plants of the new *Doritaenopsis* differ primarily from plants of 'Mei Dar Diamond' in flower color as plants of the new *Doritaenopsis* have white-colored flowers that are densely covered with variable and coalescing dark red to purplish red-colored blotches and spots whereas plants of 'Mei Dar Diamond' have purplish red-colored flowers. In addition, the labellum lateral and central lobes are fused in plants of the new *Doritaenopsis* whereas the lateral and central lobes of the labellum of plants of 'Mei Dar Diamond' are not fused.

Plants of the new *Doritaenopsis* can be compared to plants of the male parent, 'Luchia Pink'. Plants of the new *Doritaenopsis* differ primarily from plants of 'Luchia Pink' in flower color as plants of the new *Doritaenopsis* have white-colored flowers that are densely covered with variable and coalescing dark red to purplish red-colored blotches and spots whereas plants of 'Luchia Pink' have violet-colored flowers. In addition, the labellum lateral and central lobes are fused in plants of the new *Doritaenopsis* whereas the lateral and central lobes of the labellum of plants of 'Luchia Pink' are not fused.

Plants of the new *Doritaenopsis* can be compared to plants of *Phalaenopsis hybrida* 'Speechless Elegance', disclosed in U.S. Provisional Patent application Ser. No. 62/705,003 and in a U.S. Plant patent application Ser. No. 17/339,967 filed concurrently. In side-by-side comparisons, plants of the new *Doritaenopsis* differ primarily from plants of 'Speechless Elegance' in flower shape as flower petals of plants of the new *Doritaenopsis* are not as overlapping as flower petals of plants of 'Speechless Elegance'. In addition, petal blotches and spots of plants of the new *Doritaenopsis* are less distinct and more coalescing than petal blotches and spots of plants of 'Speechless Elegance'.

BRIEF DESCRIPTION OF THE PHOTOGRAPHS

The accompanying photographs illustrate the overall appearance of the new *Doritaenopsis* plant showing the colors as true as it is reasonably possible to obtain in colored reproductions of this type. Colors in the photographs may differ slightly from the color values cited in the detailed botanical description which accurately describe the colors of the new *Doritaenopsis* plant.

The photograph on the first sheet (FIG. 1) is a side perspective view of a typical flowering plant of 'Untold Stories' grown in a container.

Figure 2:
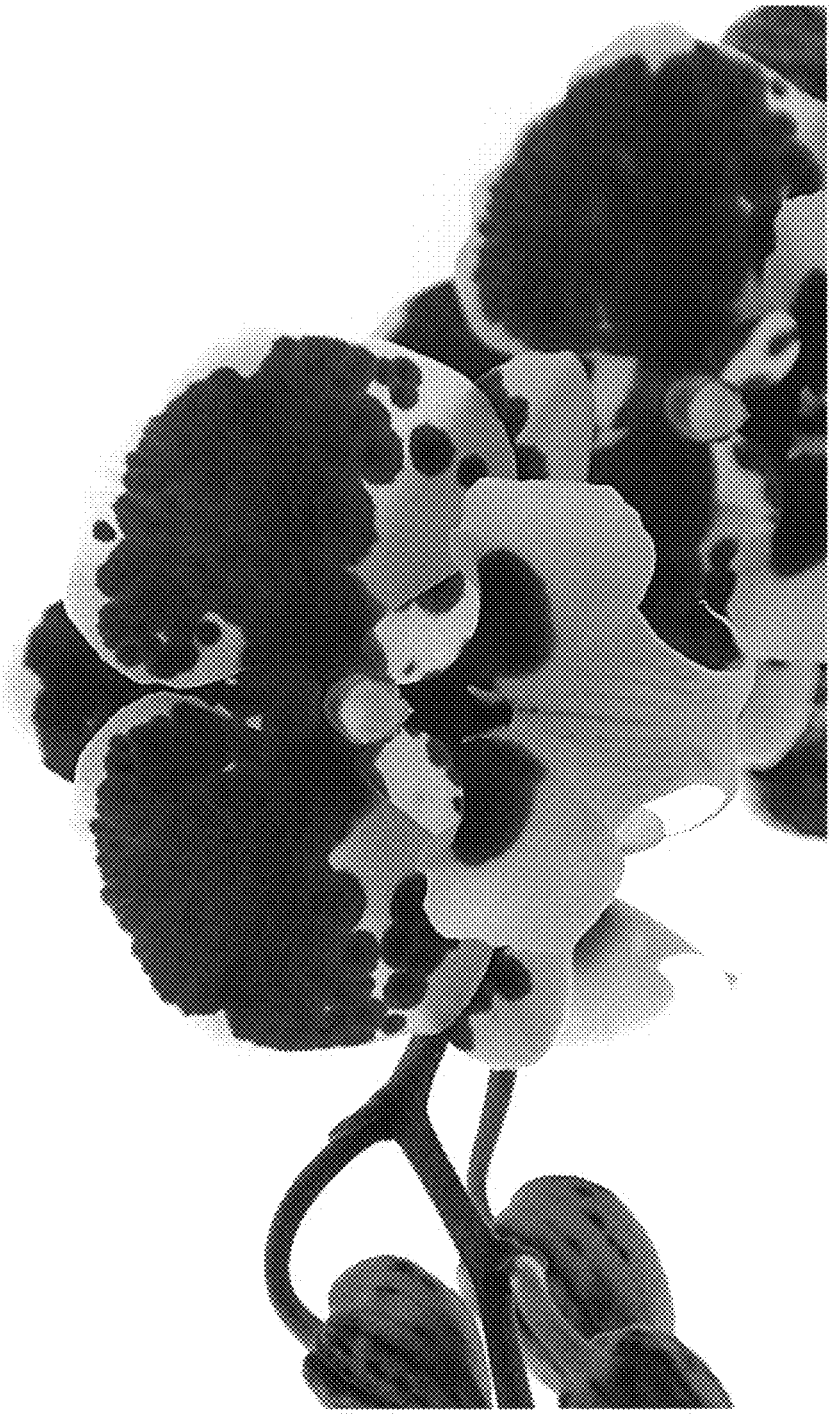

The photograph on the second sheet (FIG. 2) is a close-up view of a typical flower of 'Untold Stories'.

DETAILED BOTANICAL DESCRIPTION

The aforementioned photographs and following observations and measurements describe plants grown during the summer in 10.5-cm containers in a glass-covered greenhouse in Heemskerk, The Netherlands and under cultural practices typically used in commercial *Doritaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: x *Doritaenopsis* (*Doritis* x *Phalaenopsis*) 'Untold Stories'.

Parentage:

*Female parent*.—x *Doritaenopsis* (*Doritis* x *Phalaenopsis*) 'Mei Dar Diamond', not patented.

*Male parent*.—x *Doritaenopsis* (*Doritis* x *Phalaenopsis*) 'Luchia Pink', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 8.7 cm.

*Plant height, substrate level to top of inflorescences*.—About 55.8 cm.

*Plant diameter or spread*.—About 30 cm.

Leaf description:

*Arrangement and quantity*.—Distichous, simple; sessile; about seven leaves per plant.

*Length*.—About 17.9 cm.

*Width*.—About 6.4 cm.

*Aspect*.—Upright to outwardly arching.

*Shape*.—Narrowly obovate to narrowly oblong; slightly to moderately carinate.

*Apex*.—Unequal acute.

*Base*.—Sheathing. Sheath length: About 1.7 cm. Sheath width: About 1.4 cm. Sheath color: Close to 144A; distal margin, slightly tinged with close to 199A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Slightly darker than between 137A and 146A. Developing leaves, lower surface: Close to 146B; margin edges, close to NN137B. Fully expanded leaves, upper surface: Close to 137A; margin edges, close to 146C to 146D; venation, close to NN137B. Fully expanded leaves, lower surface: Close to 146B; margin edges, close to 146A; venation, close to 144A.

Inflorescence description:

*Appearance and flowering habit*.—Showy zygomorphic flowers arranged on axillary branched racemes; typically two inflorescences per plant; each inflorescence with about 20 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 30.2 cm.

*Inflorescence width*.—About 20 cm.

*Flower buds*.—Height: About 1.9 cm. Diameter: About 1.7 cm by 1.7 cm. Shape: Broadly ovate. Color: Close to 145B to 145C with dense blotches and dots, close to 79A and N186A.

*Flower size*.—About 7 cm (vertical) by 7.1 cm (horizontal).

*Flower depth*.—About 2.6 cm.

*Petals, quantity and arrangement*.—Three, two lateral petals and one center petal transformed into a labellum.

*Lateral petals*.—Length: About 3.5 cm. Width: About 4.8 cm. Shape: Lunate to reniform. Apex: Rounded. Margin: Entire. Texture and luster, upper and lower surfaces: Smooth, glabrous, velvety; matte. Color: When opening, upper surface: Close to NN155D densely covered with variable and coalescing blotches and spots, close to 59A, 64A, 187A and 187B; at the base (at column connection), close to 187B. When opening, lower surface: Close to 155A densely covered with variable and coalescing blotches and spots, close to 59A and 187B. Fully opened, upper surface: Close to NN155D densely covered with variable and coalescing blotches and spots, close to 59A, 72A, 72B and 187B; at the base (at column connection), close to 187B; color does not change with development. Fully opened, lower surface: Close to NN155D densely covered with variable and coalescing blotches and spots, close to 70A and N77B; color does not change with development.

*Labella*.—Appearance: Lateral and central lobes fused towards the base into a single lobe, typically referred to as a "big lip" type. Length: About 3.4 cm. Width: About 4.5 cm. Shape: Rhomboidal. Apex: Obtuse to cleft with two narrow and strongly recurved cirrose tips, about 1.3 cm in length and about 1 mm in width. Margins: Entire; slightly undulate. Texture and luster, upper and lower surfaces: Smooth, glabrous, moderately velvety; matte. Callosities: Located at the base of the labellum and attachment point of the lateral petals; about 4 mm in length, about 6 mm in width and about 7 mm in height. Color: When opening, upper surface: Close to NN155D; upper margins of central lobe and lower margins of lateral lobes, close to 150B; towards the base, close to 59A, 187A and 187B; central vein, close to 75A; callosities, close to 150B. When opening, lower surface: Close to NN155B; upper margins of central lobe and lower margins of lateral lobes, close to 150C; towards the base, close to N79B and N79C; central vein, close to 75B. Fully opened, upper surface: Close to NN155D; upper margins of central lobe and lower margins of lateral lobes, close to 150D; towards the base, close to 59A and 70A; central vein, close to 75A; callosities, close to 150B. Fully opened, lower surface: Close to NN155D; towards the base, close to N79B and N79C; central vein, close to 75C.

*Sepals*.—Quantity and arrangement: Three, one upper dorsal sepal and two lower lateral sepals. Length, dorsal sepal: About 3.75 cm. Width, dorsal sepal: About 2.4 cm. Length, lateral sepals: About 3.75 cm. Width, lateral sepals: About 2.3 cm. Shape, dorsal sepal: Short oblong to elliptic. Shape, lateral sepals: Ovate. Apex, dorsal sepal: Obtuse. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to NN155C densely covered with variable and coalescing blotches and spots, close to 59A, 187A and 187B; at the base (at column connection), close to 71A. When opening, lower surface: Close to 145C to 145D densely covered with variable and coalescing blotches and spots, close to 187A and 187B; margins and venation, close to 187A and 187B. Fully opened, upper surface: Close to NN155D densely covered with variable and coalescing blotches and spots, close to 59A, 61A, 71A and 187A; at the base (at column connection), close to 71A. Fully opened, lower surface: Close to N155B densely covered with variable and coalescing blotches and spots, close to 71A and NN77B; margins and venation, close to 71A and NN77B. Color, lateral sepals: When opening, upper surface: Close to NN155C and 150D densely covered with variable and coalescing blotches and spots, close to 59A, 71A, 187A and 187B. When opening, lower surface:

Close to 145B to 150D densely covered with variable and coalescing blotches and spots, close to 187A and 187B; margins, close to 187A and 187B. Fully opened, upper surface: Close to NN155C densely covered with variable and coalescing blotches and spots, close to 59A, 61A, 71A and 187A; at the base (at column connection), close to 150D. Fully opened, lower surface: Close to NN155B and towards the base, close to 150D densely covered with variable and coalescing blotches and spots, close to 71A and 72B; margins and venation, close to 71A and 72B.

*Peduncles*.—Length: About 56.4 cm. Diameter: About 5.5 mm. Strength: Strong. Aspect: Upright to outwardly arching. Texture and luster: Smooth, glabrous; matte. Color: Close to between 147A and 148A; fine dots, close to 143C.

*Pedicels*.—Length: About 3.9 cm. Diameter: About 3 mm. Strength: Moderately strong. Aspect: About 70° from peduncle axis. Texture and luster: Smooth, glabrous; matte. Color: Close to 145B; distally, close to N155C and proximally, close to 145A tinged with close to N77B.

*Reproductive organs*.—Androecium: Column length: About 1 cm. Column width: About 6 mm. Column color: Close to N78B and N78C; distally, close to NN155D. Pollinia quantity: Two. Pollinia diameter (per two pollinia): About 2.5 mm. Pollinia color: Close to 23A. Gynoecium: Stigma length: About 2 mm. Stigma width: About 4 mm. Stigma shape: Reniform. Stigma color: Close to N155A with margins, close to N78A. Ovary length: About 9 mm. Ovary diameter: About 1 mm. Ovary color: Close to N144D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° C. to about 40° C. and are suitable for USDA Hardiness Zones 10 to 12.

It is claimed:

1. A new and distinct *Doritaenopsis* plant named 'Untold Stories' as illustrated and described.

* * * * *